Feb. 11, 1964 J. ERRERA Plant Pat. 2,360
PEACH TREE
Filed Sept. 28, 1962
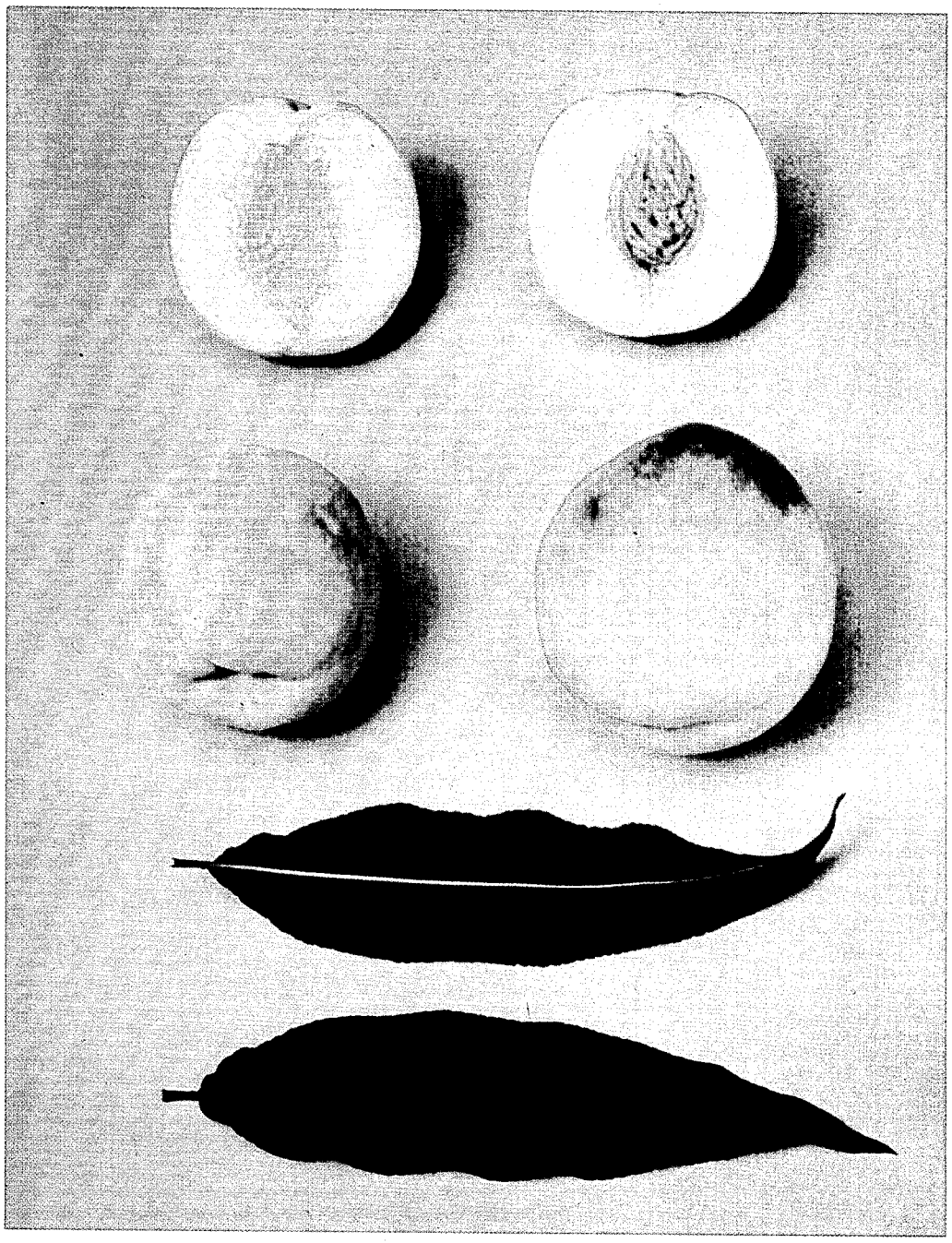
Inventor.
John Errera
By: Robb & Robb
Attorneys United States Patent Office Plant Pat. 2,360
Patented Feb. 11, 1964

2,360
PEACH TREE

John Errera, Hammonton, N.J., assignor to Edgar H. Kemp and Homer S. Kemp, both of Princess Anne, Md., trading as Bountiful Ridge Nurseries, co-partners Filed Sept. 28, 1962, Ser. No. 227,095
1 Claim. (Cl. Plt.—43)

The present invention relates to a new and distinct variety of peach tree which was discovered by me in my cultivated orchard near Hammonton, in the county of Atlantic, State of New Jersey, said new variety originating as a limb sport of the variety known as Redhaven (unpatented).

At the time of my initial discovery of the new sport, I was growing trees of the Redhaven variety in my orchard aforementioned, and in the course of my care and cultivation of this orchard, I found that a limb of one tree of the Redhaven variety bore fruit which differed in a number of respects from the normal fruit of Redhaven. Continued observation of this fruit convinced me that the Redhaven tree had sported, and I therefore carefully preserved the sport limb, continued to keep it under close observation, as well as asexual reproductions thereof derived from budwood taken from the original sport limb. As the result of the foregoing, I found that the new variety is endowed with the following unique combination of outstanding characteristics which distinguish the same from the parent variety Redhaven, as well as from all other varieties of which I am aware:

(1) A vigorous habit of growth;
(2) Good hardiness;
(3) Good disease and insect resistance;
(4) Good productivity of yellow-fleshed freestone fruit;
(5) Exceptionally good bruise resitsance of the fruit;
(6) Freedom from browning of the fruit flesh when cut and exposed to air;
(7) Large fruit size and substantially round fruit shape, even in the case of very young bearing trees;
(8) A fruit ripening habit of about 7 to 10 days earlier than the fruit of Redhaven;
(9) A high fruit color, almost entirely Brilliant Red, with a good Golden Yellow ground color;
(10) Unusually good eating, keeping and shipping qualities of the fruit; and
(11) Suitability for use for the fresh fruit market, and for dessert, culinary, canning and freezing uses.

One of the most unusual features of my new sport is that the fruit has a tendency to be almost free from browning of the flesh when cut and exposed to air, as confirmed by the fruit of second and third generation trees. The fruit also attains an exceptionally large size, even on very young bearing trees. While the tree growth, fruit shape and color more nearly resemble those of the parent variety than any other, the fruit of my new sport is of a more distinct freestone type than is the case with the regular Redhaven, and the fruit ripens from about 7 to 10 days earlier, which is an important advantage from a commercial standpoint. The high color of the fruit makes it especially attractive and desirable for commercial markets.

Asexual reproduction of my new variety by budding, as performed on my behalf at Princess Anne, in the county of Somerset, and State of Maryland, shows that the foregoing characteristics and distinctions come true to form and are established and transmitted through succeeding propagations.

The accompanying drawing shows typical specimens of the foliage and fruit of my new variety as depicted in color as nearly true as it is reasonably possible to make the same in a color illustration of this character, said fruit being shown in elevation and also in cross-section, with one half-section exposing the cavity and the other half-section exposing the stone seated in the cavity, and the foliage specimens depicting both the upper and under surfaces of typical leaves.

The following is a detailed description of the new variety, with color terminology in accordance with Maerz and Paul Dictionary of Color, except where general color terms of ordinary dictionary significance are obvious:

Locality where grown and observed: Princess Anne, Maryland.

Dates of first and last pickings: About July 15 and July 22, respectively.

Tree: Large; vigorous; spreading; from dense to open; round-topped; hardy; very productive; regular bearer.

*Trunk.*—Stocky; smooth.

*Branches.*—Stocky; smooth; glossy. Color—reddish brown, ranging from Autumn Oak, Plate 7, H–9 to Brown, Plate 15, J–9. Lenticels—few; large.

*Leaves.*—Medium thickness; rugose. Size—medium; length—from 5½ inches to 6½ inches; width—from 1 inch to 1⅜ inches. Shape—oval; lanceolate; acutely pointed. Color: upper side—Dark Green, Plate 24, E–8; under side—Light Green, Plate 23, J–3. Margin—glandular; crenate; coarsely serrate. Petiole—medium length; medium thickness. Glands—usually 2 on one side and 1 on the other side; alternate; large; reiniform; positioned at base of leaf blade; color—green. Stipules—none.

Flower buds: Hardy; medium size; medium length; conic; pointed; plump; appressed; pubescent.

Flowers:

*Dates of first and full bloom.*—About April 4 and April 10, respectively, with petal fall about April 14; medium earliness.

*Size.*—Medium.

*Color.*—Arbutus (pink), Plate 1, 4–B.

Fruit:

*Maturity when described.*—Eating ripe. Date—July 15.

*Size.*—From large to medium; uniform. Axial diameter—about 2¾ inches. Transverse diameter in suture plane—about 2½ inches. Diameter at right angles to suture plane—about 2½ inches.

*Form.*—Uniform; symmetrical; oblong; broadly ovoid.

*Suture.*—Distinct; shallow; extends from base to beyond apex; has slight, marked depression beyond pistil point.

*Ventral surface.*—Rounded slightly; lipped toward base; lips equal.

*Cavity.*—Flaring; abrupt; elongated in suture plane, with suture showing on both sides. Depth—about ½ inch. Breadth—about ⅝ inch. Markings—none.

*Base.*—Rounded.

*Apex.*—Short; mammiform; rounded; slightly oblique pistil point.

*Stem.*—Medium stoutness; pubescent; medium adherence to stone. Length—about ¼ inch.

*Skin.*—Thick; tough; tenacious to flesh; no tendency to crack during wet or dry seasons. Color—Red, Plate 3, K–11, with Golden Yellow ground color, Plate 9, 4–K. Down—moderate; short; doesn"t roll up when rubbed.

*Flesh.*—Color—yellow, mottled with red next to stone.

*Surface of pit cavity.*—Color—red, with yellow fibres.

*Amygdalin.*—Wanting.

*Juice.*—Moderate quantity; rich.

*Texture.*—Firm; fine; crisp; melting.
*Fibres.*—Few; fine; tender.
*Ripens.*—Evenly.
*Flavor.*—Subacid; mild; delicate.
*Aroma.*—Distinct.
*Eating quality.*—Best.

Stone: Free; parts from flesh smoothly; short fibres.
*Size.*—Medium. Length—about 1⅜ inches. Breadth—about 1½ inches. Thickness—about ⅝ inch.
*Form.*—Obovoid.
*Base.*—Oblique.
*Hilum*—Oval.
*Apex.*—Acute.
*Sides.*—Equal; curved on right and left sides.
*Surface.*—Irregularly furrowed near base; ridged toward apex; pitted throughout.
*Ridges.*—Rounded toward base.
*Pits.*—Elongated.
*Ventral edge.*—Thick; with wing toward base.
*Dorsal edge.*—Narrow; with deep, narrow groove throughout; ridges interrupted.

Insect and disease resistance: Good resistance to common insects and diseases to which peaches are normally subject in the Middle Atlantic geographic area, as determined by comparison with other varieties grown under the same cultural conditions at Princess Anne, Maryland.

Use: Market; local; dessert; culinary; canning; freezing.
Keeping quality: Good.
Shipping quality: Good.

I claim:

A new and distinct variety of peach tree of the yellow-fleshed freestone fruit-bearing class, substantially as herein shown and described; characterized as to novelty by the unique combination of a vigorous habit of growth, good hardiness, good disease and insect resistance, good fruit productivity, good resistance of the fruit to bruising and relative freedom of its flesh from browning when cut and exposed to air, a large fruit size and substantially round shape, even in the case of very young bearing trees, a fruit ripening habit of from 7 to 10 days earlier than Redhaven (unpatented), a high fruit color which is almost entirely Brilliant Red, but having a good Golden Yellow ground color, unusually good eating, keeping and shipping qualities of the fruit, and suitability of the fruit for the fresh fruit market, dessert, culinary, canning and freezing uses.

No references cited.